United States Patent [19]

Berg et al.

[11] Patent Number: 5,232,558
[45] Date of Patent: * Aug. 3, 1993

[54] SEPARATION OF 4-METHYL-2-PENTANONE FROM FORMIC ACID BY EXTRACTIVE DISTILLATION WITH DMSO

[75] Inventors: Lloyd Berg, 1314 S. 3rd Ave., Bozeman, Mont. 59715; Marc W. Paffhausen, Bozeman, Mont.

[73] Assignee: Lloyd Berg, Bozeman, Mont.

[*] Notice: The portion of the term of this patent subsequent to Mar. 2, 2010 has been disclaimed.

[21] Appl. No.: 957,945

[22] Filed: Oct. 8, 1992

[51] Int. Cl.⁵ .................. B01D 3/40; C07C 45/83; C07C 53/02
[52] U.S. Cl. ................................. 203/51; 203/56; 203/57; 203/60; 203/61; 203/62; 203/63; 203/64; 562/609; 568/410
[58] Field of Search ............... 203/57, 51, 61, 60, 203/62, 63, 56, 64; 568/410; 562/609

[56] References Cited

U.S. PATENT DOCUMENTS

| | | | |
|---|---|---|---|
| 2,954,392 | 9/1960 | Rylander | 568/410 |
| 3,013,954 | 12/1961 | Pacoud et al. | 203/62 |
| 3,265,592 | 8/1966 | Van Der Weel | 568/410 |
| 4,459,178 | 7/1984 | Berg et al. | 203/51 |
| 4,793,901 | 12/1988 | Berg et al. | 568/410 |

Primary Examiner—Wilbur Bascomb, Jr.

[57] ABSTRACT

4-Methyl-2-pentanone cannot be easily separated from formic acid by distillation because of the closeness of their boiling points. 4-Methyl-2-pentanone can be readily removed from formic acid by extractive distillation. Typical effective agents are dimethylsulfoxide (DMSO) and 2-undecanone; DMSO and octanoic acid; DMSO and hexyl acetate.

1 Claim, No Drawings

SEPARATION OF 4-METHYL-2-PENTANONE FROM FORMIC ACID BY EXTRACTIVE DISTILLATION WITH DMSO

This application is related to application Ser. No. 07/355,274, abandoned.

FIELD OF THE INVENTION

This invention relates to a method for separating 4-methyl-2-pentanone from formic acid using certain higher boiling liquids as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the stop of the column to insure that none of the extractive agent is carried over with the lowest boiling component. This usually requires that the extractive agent boil twenty Centigrade degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

4-Methyl-2-pentanone, B. P.=117° C. and formic acid, B. P.=101° C. possess an average relative volatility of about 1.3 and boil so close together that they are difficult to separate by conventional rectification. Extractive distillation would be an attractive method of effecting the separation of 4-methyl-2-pentanone from formic acid if agents can be found that (1) will enhance the relative volatility of 4-methyl-2-pentanone to formic acid and (2) are easy to recover from the formic acid, that is, form no azeotrope with formic acid and boil sufficiently above formic acid to make separation by rectification possible with only a few theoretical plates. Extractive distillation typically requires the addition of an equal amount to twice as much extractive agent as the 4-methyl-2-pentanone - formic acid on each plate of the rectification column. The extractive agent should be heated to about the same temperature as the plate on to which it is introduced. Thus extractive distillation imposes an additional heat requirements on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

Berg, U.S. Pat. No. 4,692,219 separated formic acid from acetic acid by extractive distillation. Extractive distillation was used by Berg, U.S. Pat. No. 4,735,690 to remove water and impurities from formic acid and Berg, U.S. Pat. No. 4,793,901 to break the 2-pentanone -formic acid azeotrope.

OBJECTIVE OF THE INVENTION

The object of this invention is to provide a process or method of extractive distillation that will enhance the relative volatility of 4-methyl-2-pentanone from formic acid in their separation in a rectification column. It is a further object of this invention to identify suitable extractive distillation agents that will separate the 4-methyl-2-pentanone - formic acid mixture and make possible the production of pure 4-methyl-2-pentanone and formic acid by rectification. It is a further object of this invention to identify certain amides which in addition to the above constraints, are stable, can be separated from formic acid by rectification with relatively few theoretical plates and can be recycled to the extractive distillation column and reused with little or no decomposition.

SUMMARY OF THE INVENTION

The objects of the invention are provided by a process for separating 4-methyl-2-pentanone from formic acid which entails the use of dimethylsulfoxide, either alone or admixed with certain oxygenated organic compounds as the agents in extractive distillation.

TABLE 1

| Effective Extraction Distillation Agents | | | | |
|---|---|---|---|---|
| Compounds | Ratios | | Relative Volatilities | |
| Dimetylsulfoxide (DMSO), Benzoic acid | $(1/2)^2$ | $(3/5)^2$ | 2.4 | 2.4 |
| DMSO, Octanoic acid | " | " | 3.3 | 2.4 |
| DMSO, 2-Undecanone | " | " | 2.4 | 2.6 |
| DMSO, Benzonitrile | " | " | 1.4 | 1.7 |
| DMSO, 2-Methoxyethyl ether | " | " | 1.7 | 2.1 |
| DMSO, Dipropylene glycol methyl ether acetate | " | " | 3.9 | 2.3 |
| DMSO, Ethylene glycol diacetate | " | " | 2.1 | 1.8 |
| DMSO, Hexyl acetate | " | " | 2.4 | 2.6 |
| DMSO, Ethyl phenyl acetate | " | " | 1.3 | 1.4 |
| DMSO, Isobutyl heptyl ketone | " | " | 3.2 | 1.7 |
| DMSO, Diphenyl ether | " | " | 1.7 | 1.9 |

DETAILED DESCRIPTION OF THE INVENTION

We have discovered that dimethylsulfoxide (DMSO) when admixed with other high boiling organic compounds, will effectively increase the relative volatility of 4-methyl-2-pentanone to formic acid and permit the separation of pure 4-methyl-2-pentanone from formic acid by rectification when employed as the agent in extractive distillation. Table 1 lists the mixtures containing DMSO in the proportions that we have found to be effective. The data in Table 1 was obtained in a vapor-liquid equilibrium still. In each case, the starting material was 35% 4-methyl-2-pentanone, 65% formic acid. The ratios are the parts by weight of extractive agent used per part of 4-methyl-2-pentanone - formic acid mixture. The relative volatilities are listed for each of the two ratios employed. The compounds which are effective when used in mixtures with DMSO are benzoic acid, 2-undecanone, benzonitrile, 2-methoxyethyl ether, dipropylene glycol methyl ether acetate, ethylene glycol diacetate, hexyl acetate, ethyl phenyl acetate, isobutyl heptyl ketone and diphenyl ether.

The two relative volatilities shown in Table 1 correspond to the two different ratios investigated. For example, in Table 1, one half part of DMSO plus one half part of benzoic acid with one part of the 4-methyl-2-pentanone -formic acid mixture gives a relative volatility of 2.4; 3/5 parts of DMSO plus 3/5 parts of benzoic acid give 2.4. In every example in Table 1, the starting material is the 4-methyl-2-pentanone - formic acid mixture which possesses a relative volatility of 1.3.

THE USEFULNESS OF THE INVENTION

The usefulness or utility of this invention can be demonstrated by referring to the data presented in Table 1. All of the successful extractive distillation agents show that 4-methyl-2-pentanone and formic acid can be separated from each other by means of distillation in a rectification column and that the ease of separation as measured by relative volatility is considerable. Without these extractive distillation agents, the relative volatility would be only 1.3 and separation by rectification would be difficult. The data also show that the most attractive agents will operate at a boil up rate low enough to make this a useful and efficient method of recovering high purity 4-methyl-2-pentanone and formic acid from any mixture of these two close boiling compounds. The stability of the compounds used and the boiling point difference is such that complete recovery and recycle is obtainable by a simple distillation and the amount required for make-up is small.

WORKING EXAMPLE

Example 1: Fifty grams of the 4-methyl-2-pentanone - formic acid mixture, 25 grams of DMSO and 25 grams of 2-undecanone were charged to a vapor-liquid equilibrium still and refluxed for five hours. Analysis indicated a vapor composition of 18.6% 4-methyl-2-pentanone, 81.4% formic acid and a liquid composition of 8.6% 4-methyl-2-pentanone, 91.4% formic acid which is a relative volatility of 2.4. Five grams of DMSO and five grams of 2-undecanone were added and refluxing continued for another 12 hours. Analysis indicated a vapor composition of 23.4% 4-methyl-2-pentanone, 76.6% formic acid and a liquid composition of 23.4% 4-methyl-2-pentanone, 89.5% formic acid which is a relative volatility of 2.6.

We claim:

1. A method for recovering 4-methyl-2-pentanone from mixtures of 4-methyl-2-pentanone and formic acid which comprises distilling a mixture of 4-methyl-2-pentanone and formic acid in a rectification column in the presence of about one part of an extractive agent per part of the 4-methyl-2-pentanone - formic acid mixture, recovering 4-methyl-2-pentanone as overhead product and obtaining the extractive agent and the formic acid from the stillpot, wherein said extractive agent comprises dimethyl sulfoxide and at least one material selected from the group consisting of benzoic acid, 2-undecanone, benzonitrile, 2-methoxyethyl ether, dipropylene glycol methyl ether acetate, hexyl acetate, ethyl phenyl acetate, isobutyl heptyl ketone and diphenyl ether.

* * * * *